(12) United States Patent
Abbas et al.

(10) Patent No.: US 12,016,620 B2
(45) Date of Patent: Jun. 25, 2024

(54) CATHETER CONSTRUCTION TO ELIMINATE STATIC AND NOISE

(71) Applicant: Biosense Webster (Israel) Ltd., Yokneam (IL)

(72) Inventors: Mohammad Abbas, Fullerton, CA (US); Ricardo Padilla, Jr., Eastvale, CA (US); Dustin R. Tobey, San Dimas, CA (US); Steven W. Wu, San Jose, CA (US); Yitzhak T. Levy, Irvine, CA (US); Raymond Yue-sing Tang, Rosemead, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 308 days.

(21) Appl. No.: 16/942,823

(22) Filed: Jul. 30, 2020

(65) Prior Publication Data

US 2021/0059744 A1 Mar. 4, 2021

Related U.S. Application Data

(60) Provisional application No. 62/895,189, filed on Sep. 3, 2019.

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 2018/00077* (2013.01); *A61B 2018/00083* (2013.01);
(Continued)

(58) Field of Classification Search
CPC ...... A61B 18/1492; A61B 2018/00077; A61B 2018/00083; A61B 2018/00136;
(Continued)

(56) References Cited

U.S. PATENT DOCUMENTS

| 5,738,096 A | 4/1998 | Ben-Haim |
| 8,956,353 B2 | 2/2015 | Govari et al. |

(Continued)

FOREIGN PATENT DOCUMENTS

| CN | 102040729 A | 5/2011 |
| GB | 2476698 A | 7/2011 |

(Continued)

OTHER PUBLICATIONS

International Search report and Written Opinion dated Nov. 27, 2020, for International Application No. PCT/IB2020/058085, 11 pages.

(Continued)

*Primary Examiner* — Linda C Dvorak
*Assistant Examiner* — Abigail Bock
(74) *Attorney, Agent, or Firm* — Frost Brown Todd LLP

(57) ABSTRACT

An apparatus includes a catheter having a flexible outer sheath and a flexible irrigation tube. The flexible outer sheath defines a first lumen. The flexible irrigation tube is positioned inside the first lumen and includes an inner layer and an outer coating layer. The inner layer is formed of a synthetic polymer compound and has a uniform cross-section with a hollow interior defining a second lumen. The outer coating layer is disposed around the inner layer. The outer coating layer is formed of a polymeric compound and includes first and second isomers. The first isomer is configured to carry a positive electric charge and the second isomer is configured to carry a negative electric charge.

20 Claims, 8 Drawing Sheets

(52) U.S. Cl.
CPC ............... *A61B 2018/00136* (2013.01); *A61B 2018/00577* (2013.01); *A61B 2018/1253* (2013.01); *A61B 2018/126* (2013.01); *A61B 2218/002* (2013.01)

(58) Field of Classification Search
CPC .. A61B 2018/00577; A61B 2018/1253; A61B 2018/126; A61B 2218/002; A61M 2205/0233
See application file for complete search history.

(56) References Cited

U.S. PATENT DOCUMENTS

| | | | |
|---|---|---|---|
| 9,480,416 | B2 | 11/2016 | Govari et al. |
| 9,801,585 | B2 | 10/2017 | Shah et al. |
| 9,907,480 | B2 | 3/2018 | Basu et al. |
| 10,130,422 | B2 | 11/2018 | Ditter |
| 2010/0217257 | A1 | 8/2010 | Howat et al. |
| 2010/0249602 | A1 | 9/2010 | Buckley et al. |
| 2013/0030426 | A1 | 1/2013 | Gallardo et al. |
| 2017/0003256 | A1* | 1/2017 | Ziegler ................ F16L 11/127 |
| 2017/0312022 | A1 | 11/2017 | Beeckler et al. |
| 2018/0056038 | A1 | 3/2018 | Aujla et al. |
| 2018/0071017 | A1 | 3/2018 | Bar-Tal et al. |
| 2018/0117239 | A1* | 5/2018 | Schmidt ............... B29C 63/0069 |
| 2018/0140355 | A1 | 5/2018 | Howat et al. |
| 2018/0263688 | A1* | 9/2018 | Barrish ................ A61B 5/6853 |
| 2021/0212754 | A1* | 7/2021 | Olson ................ A61B 18/1492 |

FOREIGN PATENT DOCUMENTS

| | | | |
|---|---|---|---|
| JP | 5009974 | B2 | 8/2012 |
| WO | WO-2011038353 | A2 * | 3/2011 ............... A61F 2/06 |
| WO | WO 2018/170537 | A1 | 9/2018 |

OTHER PUBLICATIONS

Chinese First Office Action and Search Report dated Feb. 23, 2024, for Application No. 202080062360.8, 9 pages.
Chinese Second Office Action dated Apr. 12, 2024, for Application No. 202080062360.8, 8 pages.
Japanese First Office Action dated Mar. 5, 2024, for Application No. 2022-514203, 3 pages.

* cited by examiner

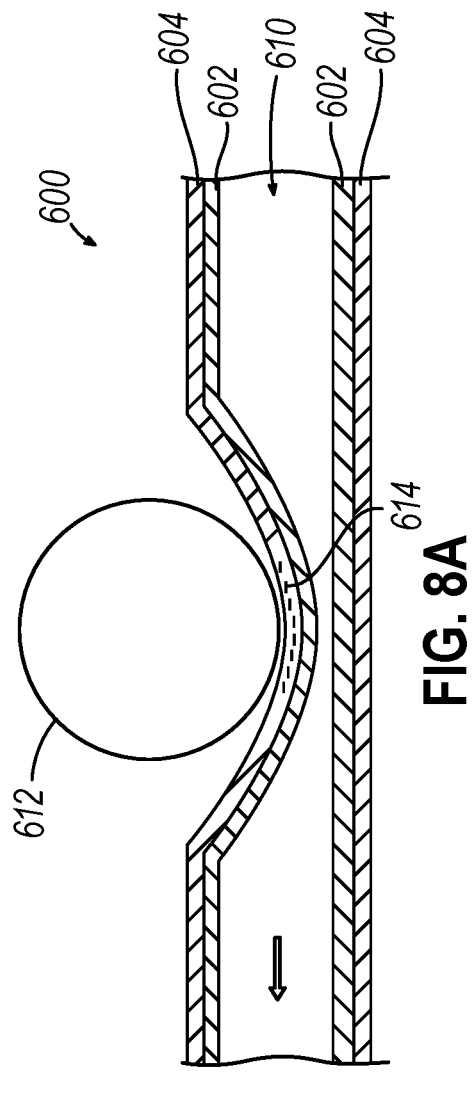
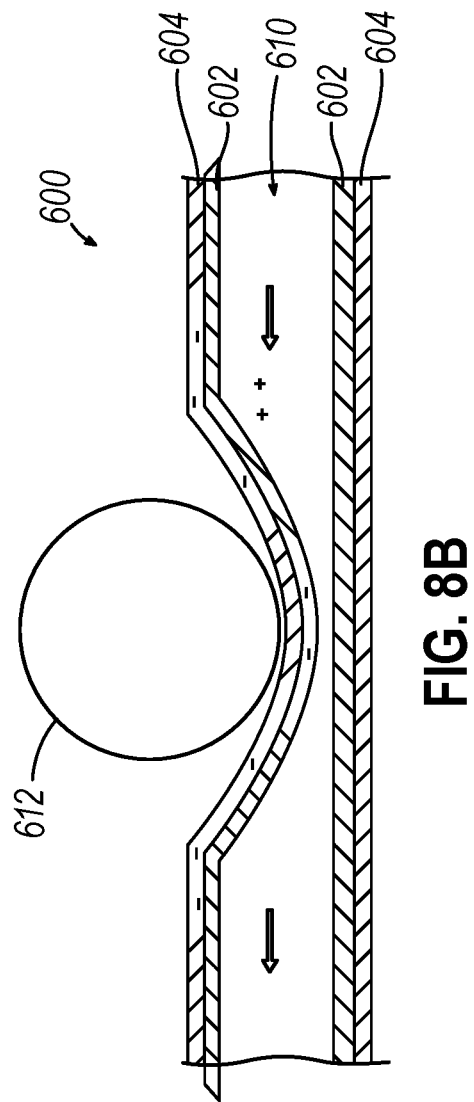

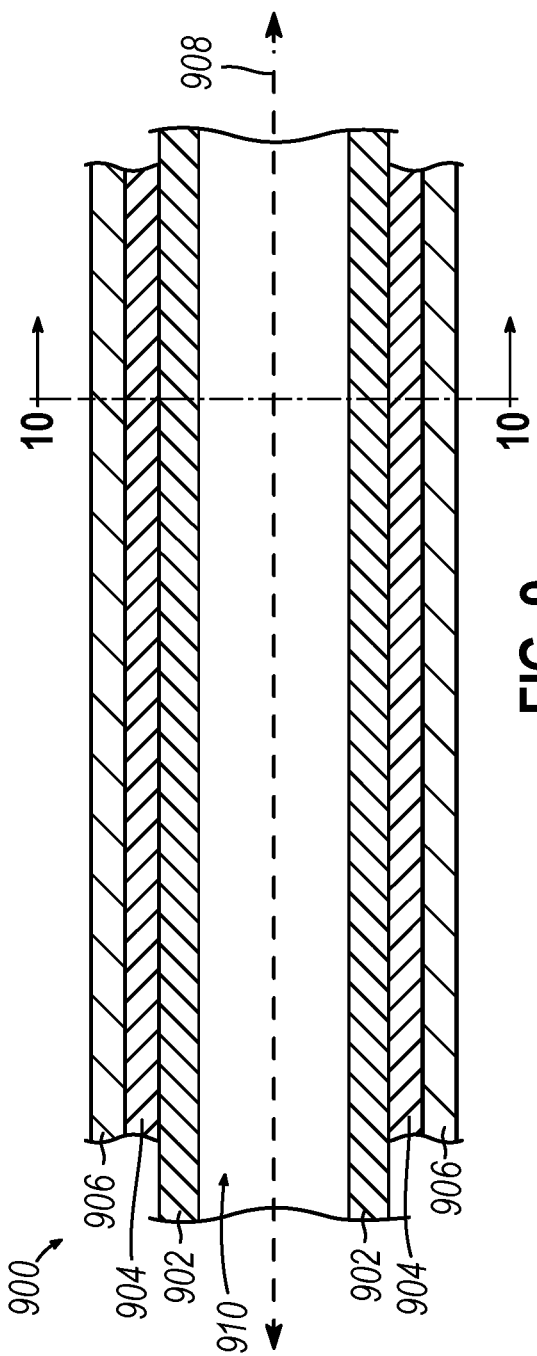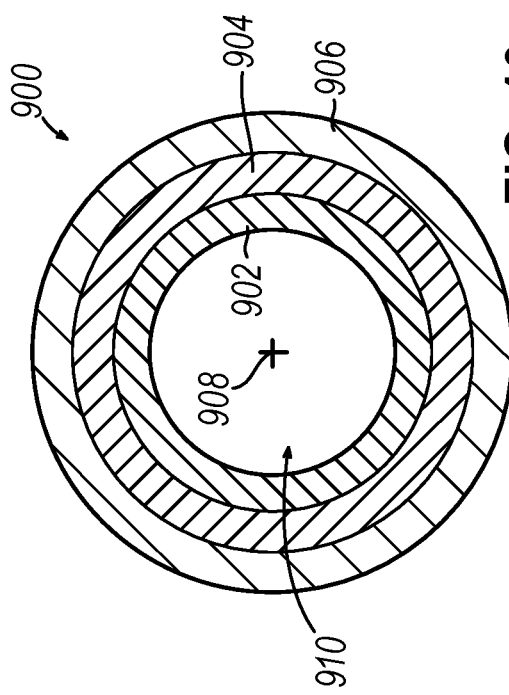

CATHETER CONSTRUCTION TO ELIMINATE STATIC AND NOISE

PRIORITY

This application claims priority to U.S. Provisional Pat. App. No. 62/895,189, entitled "Catheter Construction to Eliminate Static and Noise," filed Sep. 3, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein in its entirety; U.S. Pub. No. 2017/0312022, entitled "Irrigated Balloon Catheter with Flexible Circuit Electrode Assembly," published Nov. 2, 2017, the disclosure of which is incorporated by reference herein in its entirety; U.S. Pub. No. 2018/0071017, entitled "Ablation Catheter with a Flexible Printed Circuit Board," published Mar. 15, 2018, the disclosure of which is incorporated by reference herein in its entirety; U.S. Pub. No. 2018/0056038, entitled "Catheter with Bipole Electrode Spacer and Related Methods," published Mar. 1, 2018, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; U.S. Pat. No. 8,956,353, entitled "Electrode Irrigation Using Micro-Jets," issued Feb. 17, 2015, the disclosure of which is incorporated by reference herein in its entirety; and U.S. Pat. No. 9,801,585, entitled "Electrocardiogram Noise Reduction," issued Oct. 31, 2017, the disclosure of which is incorporated by reference herein in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; and U.S. Pub. No. 2018/0056038, entitled "Catheter with Bipole Electrode Spacer and Related Methods," published Mar. 1, 2018, the disclosure of which is incorporated by reference herein in its entirety.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

FIG. 8A depicts a longitudinal cross-sectional view of the irrigation tube of FIG. 6 in use and having an illustrative initial static charge buildup adjacent an irrigation pump roller, where the irrigation tube includes multiple material layers;

FIG. 8B depicts the irrigation tube of FIG. 8A, showing the static charge buildup absorbed by the multiple material layers;

FIG. 9 depicts a longitudinal cross-sectional view of a second example of an irrigation tube, which may be used with a variation of the catheter of FIG. 1, where the second embodiment of the irrigation tube includes multiple material layers; and FIG. 10 depicts a transverse cross-sectional view of the irrigation tube of FIG. 9 taken along centerline 10-10 of FIG. 9.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. OVERVIEW OF EXEMPLARY ABLATION CATHETER SYSTEM

Figure 1:
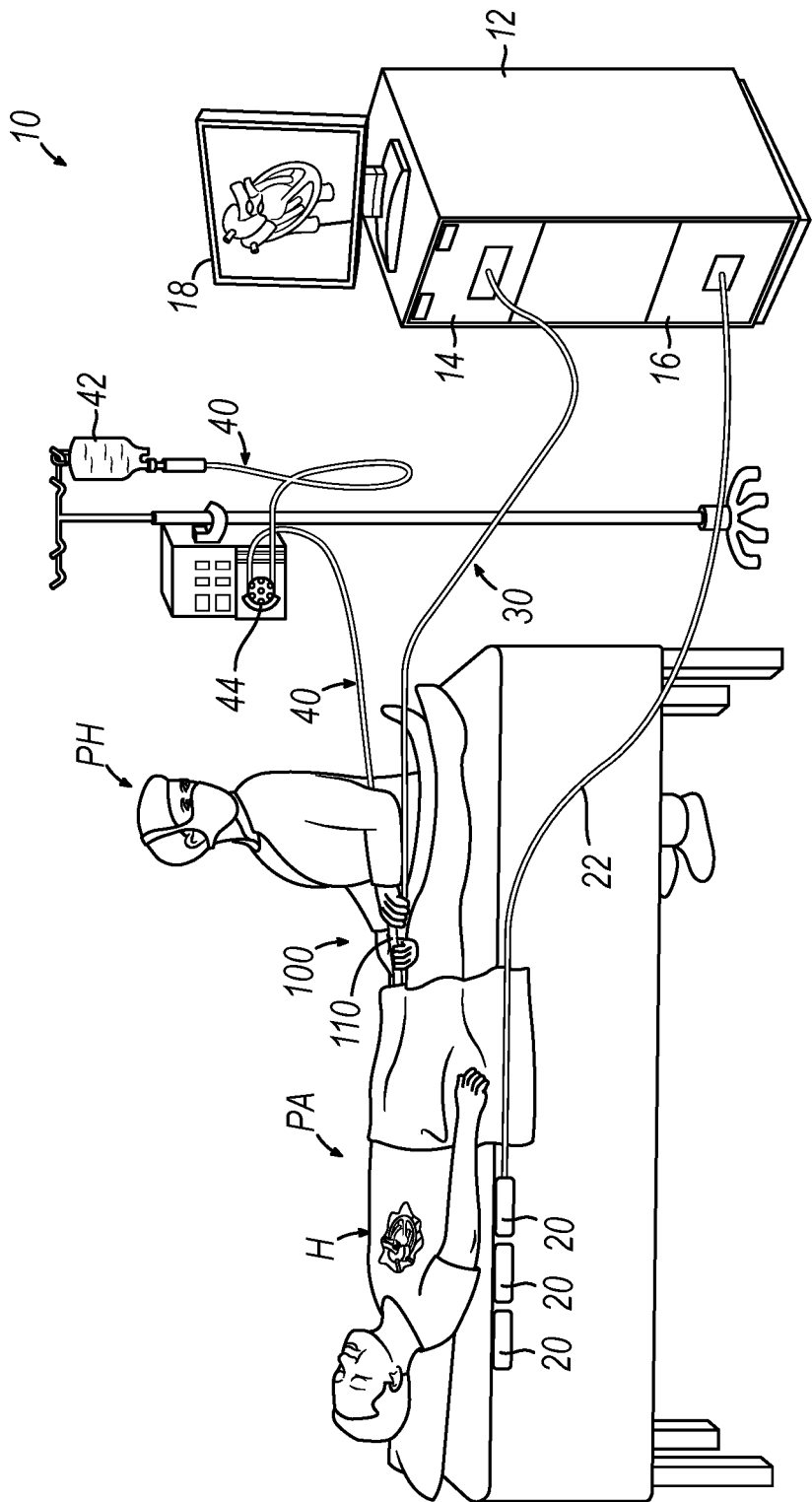
FIG. 1 depicts a schematic view of a medical procedure in which a catheter of a catheter assembly is inserted in a patient.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2 and 4 but not shown in FIG. 1) of catheter assembly (100) disposed in a patient (PA) to ablate tissue in or near the heart (H) of the patient (PA). Catheter assembly (100) includes handle (110), catheter (120) extending distally from handle (110), end effector (140) located at a distal end of catheter (120), and a user input feature (190) located on handle.

As will be described in greater detail below, end effector (140) includes various components configured to deliver RF energy to targeted tissue sites, provide EP mapping functionality, track external forces imparted on end effector (140), track the location of end effector (140), and disperse irrigation fluid. As will also be described in greater detail below, user input feature (190) is configured to deflect end effector (140) and a distal portion of catheter (120) away from a central longitudinal axis (L-L) (FIGS. 3-5) defined by a proximal portion of catheter (120).

Figure 2:
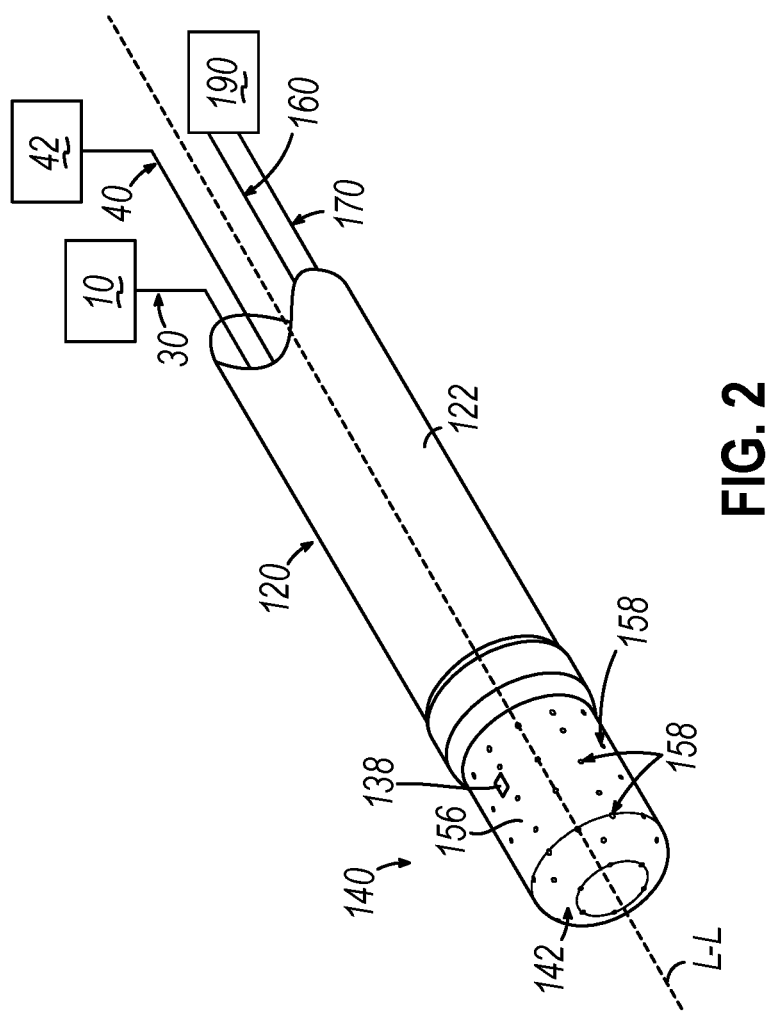
FIG. 2 depicts a perspective view of a distal portion of the catheter of FIG. 1, with additional components shown in schematic form.

As shown in FIG. 2, catheter (120) includes an elongate flexible sheath (122), with end effector (140) being disposed at a distal end of sheath (122). End effector (140) and various components that are contained in sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18), such as a digital display. Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly (150) in end effector (140). In such versions, the processor of console (12) is also operable to process the position indicative signals from navigation sensor assembly (150) to thereby determine the position of end effector (140) within the patient (PA). As will be described in greater detail below, navigation sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a navigation sensor assembly (150).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from navigation sensor assembly (150) of end effector (140). For instance, as end effector (140) of catheter (120) moves within the patient (PA), the corresponding position data from navigation sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). The processor of console (12) may also drive display (18) to superimpose the current location of end effector (140) on the images of the patient's anatomy, such as by superimposing an illuminated dot, a crosshair, a graphical representation of end effector (140), or some other form of visual indication.

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. EXEMPLARY END EFFECTOR OF CATHETER ASSEMBLY

Figure 3:
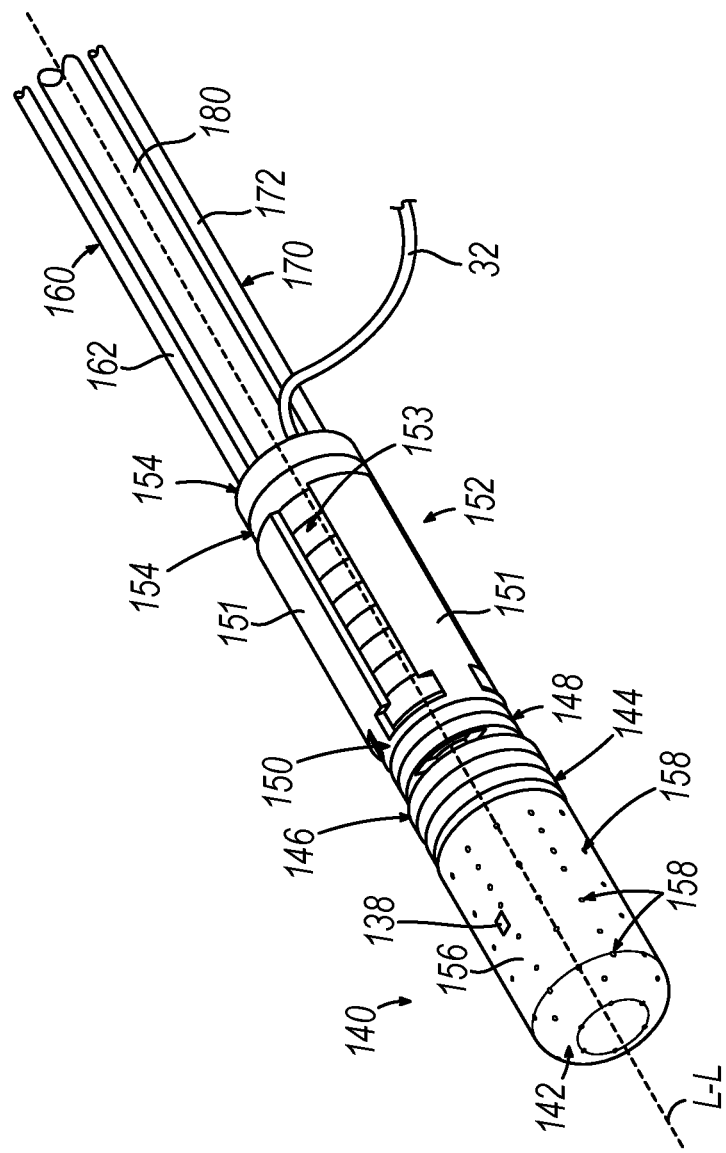
FIG. 3 depicts a perspective view of the distal portion of the catheter of FIG. 1, with an outer sheath omitted to reveal internal components.
Figure 4:
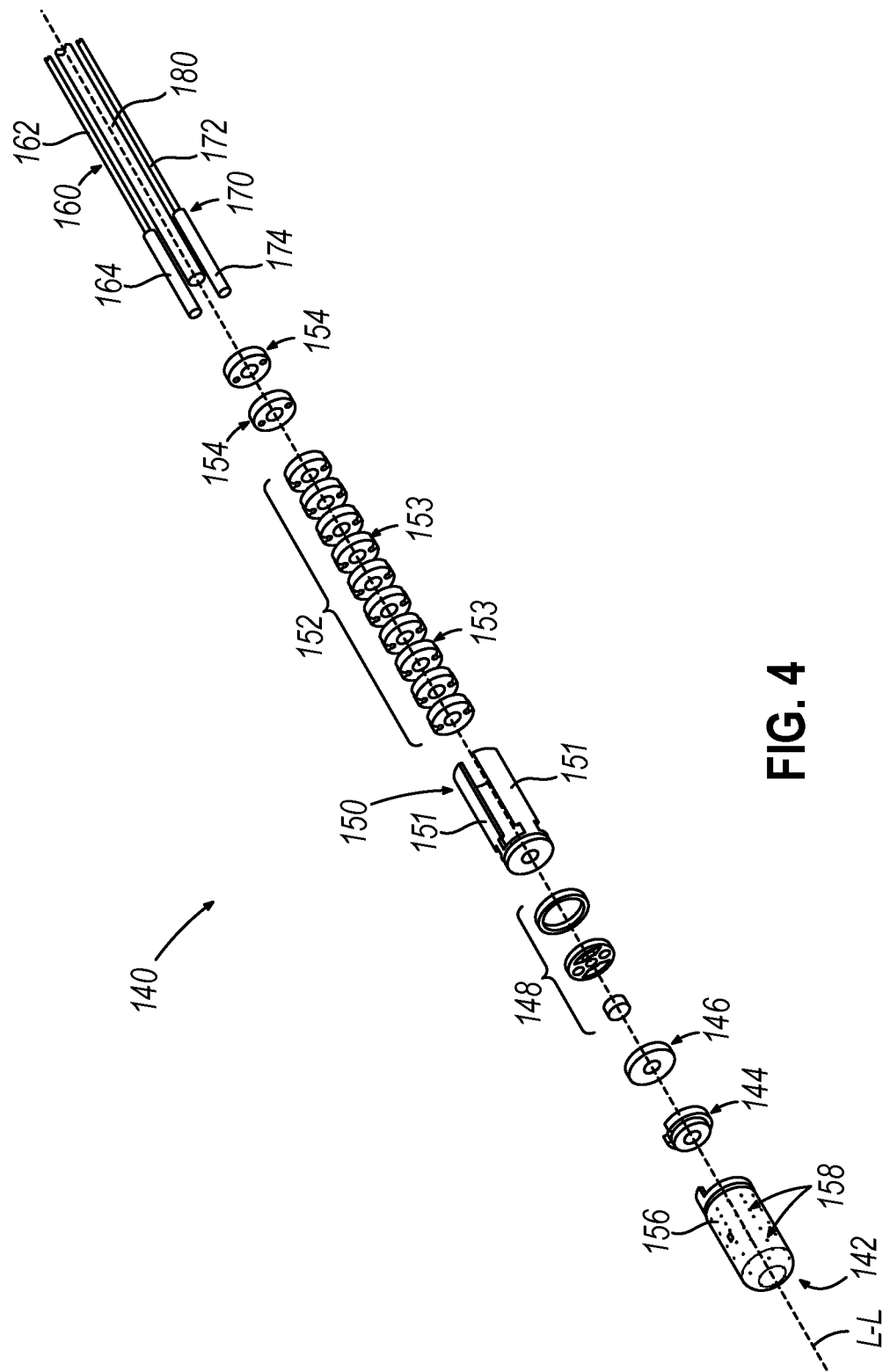
FIG. 4 depicts an exploded perspective view of the distal portion of the catheter of FIG. 1.

FIGS. 2-4 show exemplary components of end effector (140), and other components of the distal portion of catheter (120), in greater detail. End effector (140) includes a distal tip member (142), a distal tip base (144), a distal circuit disk (146), a strain gauge assembly (148), a navigation sensor assembly (150), a distal spacer stack (152), and a pair of proximal spacers (154). Distal tip member (142), distal tip base (144), distal circuit disk (146), strain gauge assembly (148), navigation sensor assembly (150), distal spacer stack (152), and proximal spacers (154) are coaxially aligned with each other and are stacked longitudinally so that these components (144-154) define a stacked circuit. A pair of push-pull cables (160, 170) and an irrigation tube (180) extend along the length of catheter (120) to reach end effector (140). Each of the foregoing components will be described in greater detail below. Flexible sheath (122) surrounds all of the foregoing components except for distal tip member (142).

As shown in FIGS. 3-4, distal tip member (142) of the present example is electrically conductive and includes a cylindraceous body (156) with a dome tip. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximal-most spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). First driver module (14) may process the EP mapping signals and provide the physician (PH) with corresponding feedback indicating the locations of aberrant electrical activity in accordance with the teachings of various references cited herein.

Strain gauge assembly (148) is positioned proximal to distal circuit disk (146) and is configured to sense external forces that impinge against distal tip member (142). When distal tip (142) encounters external forces (e.g., when distal tip (142) is pressed against tissue), those external forces are communicated from distal tip (142) to distal tip base (144), to distal circuit disk (146), and to strain gauge assembly (148) such that strain gauge may generate a suitable signal corresponding to the magnitude and direction of the external force.

Navigation sensor assembly (150) may generate signals indicating the position and orientation of end effector (140) in three-dimensional space with substantial precision. The signals from navigation sensor assembly (150) may be communicated through vias or other structures in the layers that are proximal to strain navigation sensor assembly (150), eventually reaching first driver module (14) of console (12) via cable (30).

As noted above and as shown in FIGS. 1-2, cable (30) couples catheter assembly (100) with drive system (10). As shown in FIG. 4, wires (32) of cable (30) extend along the length of catheter (120) to reach the proximal-most proximal spacer (154).

As also noted above, catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 3-4. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through the central passageway formed by the aligned by the above-mentioned central apertures, ultimately reaching the interior of distal tip member (142) via aperture (158) of distal tip base (144).

As noted above, and as shown in FIGS. 2-4, catheter (100) of the present example further includes a pair of push-pull cables (160, 170). Push-pull cables (160, 170) enable the physician (PH) to selectively deflect end effector (140) laterally away from a longitudinal axis (L-L), thereby enabling the physician (PH) to actively steer end effector (140) within the patient (PA). Various mechanisms that may be used to drive push-pull cables (160, 170) in a simultaneous, longitudinally-opposing fashion will be apparent to those skilled in the art in view of the teachings herein.

III. EXEMPLARY CATHETER CONSTRUCTION TO ELIMINATE STATIC AND NOISE

As mentioned above, distal tip (142) of end effector (140) defines a plurality of openings (158) configured to allow irrigation fluid to be communicated from the interior to the exterior of distal tip member (142). As also mentioned above, end effector (140) is configured to be disposed within or near the heart (H) of the patient (PA) to ablate tissue. Therefore, during exemplary use, pump (44) may drive irrigation fluid from fluid source (42), through conduit (40) and irrigation tube (180), and into the interior of distal tip member (142) such that irrigation fluid originating from fluid source (42) may flow out of the plurality of openings (158) into or near the heart (H) of the patient (PA). Irrigation fluid may be used during exemplary use of catheter assembly (100) to sufficiently cool end effector (140) or surrounding tissue in response to activating end effector (140) with RF energy in accordance with the description above.

One type of pump (44) which may be utilized is a peristaltic pump. In peristaltic pumps, the irrigation fluid may be contained within a flexible tube, such as conduit (40) (shown in FIG. 1), which is fitted inside a semi-circular pump casing, often referred to as a "track." The conduit (40) is pressed against the track by a rotor with two or more rollers attached to its external circumference. As the rotor turns, the portion of the conduit (40) being compressed is occluded, or pinched closed between the roller and the track, forcing the fluid being pumped to move through the conduit (40). As the conduit (40) re-opens to its natural shape after the roller of the pump (44) passes, a vacuum is created, drawing fluid into the pump (44). The advancing roller then pushes the fluid toward the pump outlet. For some medical procedures, the conduit (40) may be built into a disposable tube set that can be discarded after each procedure, which minimizes cleaning validation.

In some catheter systems, electrical static buildup and discharge can occur on the connected irrigation tube (e.g., conduit (40) shown in FIG. 1) due to the irrigation tube contacting moving portions of the system, such as the rollers of a pump (e.g., pump (44) shown in FIG. 1). The buildup and discharge of static electricity can, in some instances, create noise in the RF system at a repeating harmonic consistent with the flowrate of the irrigation pump. Such static-based noise may adversely affect readings from the EP mapping electrodes (e.g., microelectrodes (138) shown in FIGS. 2 and 3). In addition, or in the alternative, such static-based noise may adversely affect signals generated by one or more sensors (e.g., navigation sensor assembly (150) shown in FIGS. 3 and 4). In addition, or in the alternative, such static-based noise may adversely affect delivery of ablation RF energy via ablation electrodes (e.g., cylindraceous body (156) shown in FIGS. 2 through 4).

Figure 5:
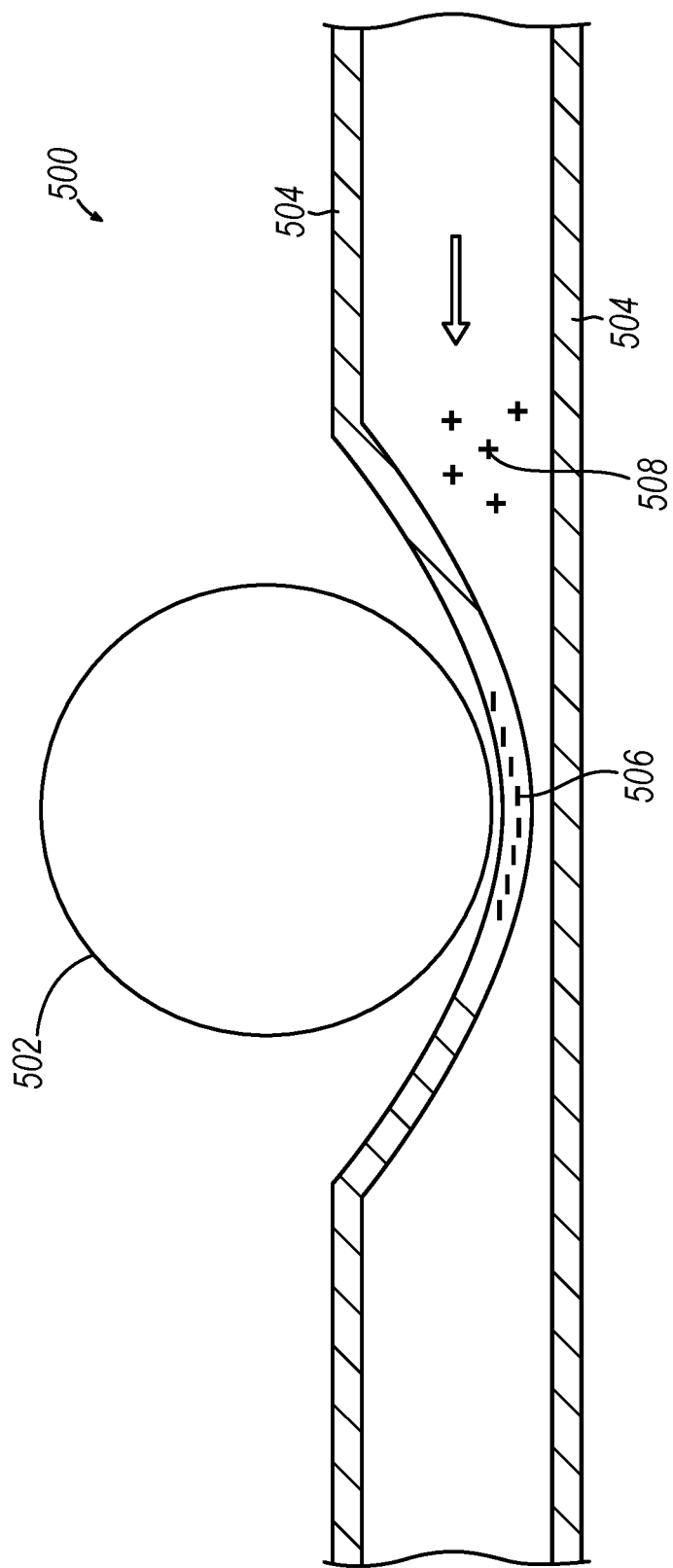
FIG. 5 depicts a longitudinal cross-sectional view of an irrigation tube of the prior art in use and having an illustrative initial static charge buildup adjacent an irrigation pump roller, where the irrigation tube includes a single material layer which collects the static charge buildup.

FIG. 5 depicts a longitudinal cross-sectional view of an irrigation tube (500) of the prior art in use and positioned adjacent a pump roller (502) of a peristaltic pump configured to drive fluid through the irrigation tube (500). The irrigation tube (500) includes a single material layer (504), such as a flexible polymer layer. Also depicted is an illustrative initial static charge buildup (506) adjacent the irrigation pump roller (502), where the single material layer (504) collects the static charge buildup (506) over time. In this prior art configuration, static charge (506) can accumulate on the irrigation tube (500) due to the triboelectric effect each time the irrigation pump roller (502) contacts it. The static charge (506) can cause spikes of electric noise driven by the frequency the pump roller (502) contacts the irrigation tube (500), the noise of which can be dictated by the opposing charged particles (508) provided by the irrigation flow through the irrigation tube (500).

Figure 6:
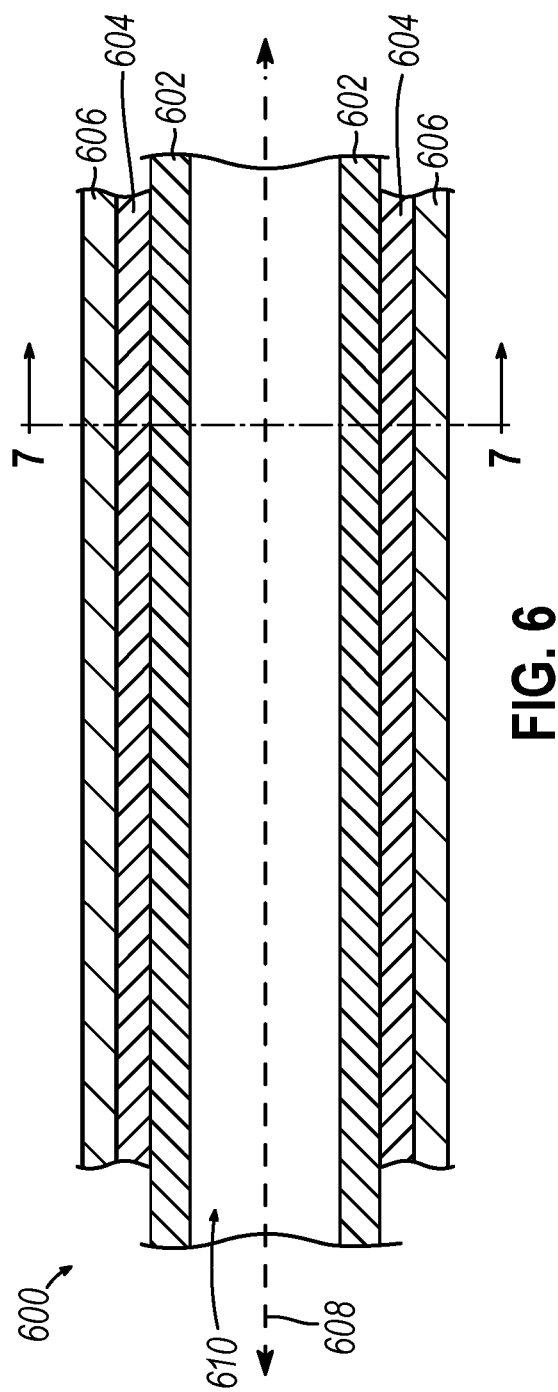
FIG. 6 depicts a longitudinal cross-sectional view of a first example of an irrigation tube, which may be used with a variation of the catheter of FIG. 1, where the first embodiment of the irrigation tube includes multiple material layers.
Figure 7:
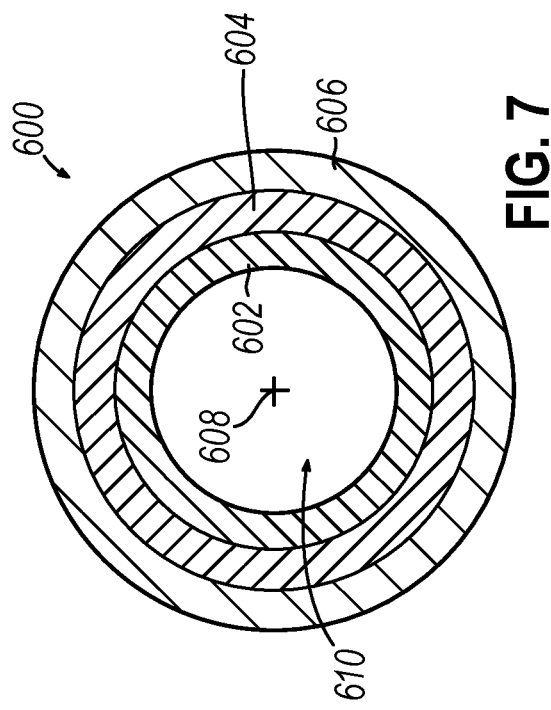
FIG. 7 depicts a transverse cross-sectional view of the irrigation tube of FIG. 6 taken along centerline 7-7 of FIG. 6.

To minimize the buildup and discharge of static electricity, and decrease any electrical noise caused by the static electricity, one or more polymeric coatings can be applied to the irrigation tube. FIGS. 6-7 depict one example of a medical irrigation tube (600), which may be used with a variation of the catheter assembly (100) of FIG. 1. For example, irrigation tube (600) may be used in place of conduit (40), and may similarly couple with a pump (e.g., pump (44)) to transport irrigation fluid from a fluid source (e.g., fluid source (42)) to a patient (PA). Irrigation tube (600) of this example includes multiple flexible material layers, including a base or inner layer (602) and a coating layer (604). Optionally, irrigation tube (600) can include an additional wear-resistant layer (606), which may coat a portion or all of irrigation tube (600); and may be applied to cover the coating layer (604).

In some versions, the inner layer (602) is formed of a flexible synthetic plastic polymer, for example, polyvinyl chloride (PVC). The inner layer (602) may be, for example, extruded or otherwise manufactured to form a hollow cylindrical tube defining a central longitudinal axis (608). The hollow inner portion (610) can function as a lumen or irrigation channel to transport fluid, such as between fluid source (42) and patient (PA).

The outer coating layer (604) is formed of a conductive polymer composed of one or more polymers or ionomers, for example, poly(3,4-ethylenedioxythiophene)-poly(styrenesulfonate) (PEDOT:PSS). PEDOT:PSS is a polymer mixture of two polymers or ionomers. One component in this mixture is made up of sodium polystyrene sulfonate which is a sulfonated polystyrene. Part of the sulfonyl groups are deprotonated and carry a negative charge. The other component, poly(3,4-ethylenedioxythiophene), is a conjugated polymer and carries positive charges and is based on polythiophene. PEDOT:PSS can be made highly conductive or highly resistive, optically transparent (e.g., from approximately 65 to approximately 90%), and slightly elastic.

The wear-resistant layer (606) can be formed of, for example, polyurethane, polyolefin, or another polymer having similar properties. The wear-resistant layer (606) may coat a portion of the irrigation tube (600), such as the portion adjacent a peristaltic pump roller (502) or any other area which may experience greater wear during use.

FIG. 8A depicts a longitudinal cross-sectional view of the irrigation tube (600) of FIGS. 6-7 in use and positioned adjacent a pump roller (612) of a peristaltic pump that is configured to drive fluid through the irrigation tube (600). The irrigation tube (600) includes two material layers: the inner layer (602) and the outer coating layer (604). While it is not shown, the irrigation tube (600) may optionally include a wear-resistant layer, such as wear-resistant layer (606) as described above.

Also depicted in. FIG. 8A is an illustrative initial static charge buildup (614) adjacent the irrigation pump roller (612), where the outer coating layer (604) receives the static charge buildup (614) as the pump roller (612) contacts the irrigation tube (600). In this exemplary configuration, static charge (614) can accumulate on the irrigation tube (600) due to the triboelectric effect each time the irrigation pump roller (612) contacts it. However, as depicted in FIG. 8B, the highly resistive formulation of PEDOT:PSS of the outer coating layer (604) can be used as a dissipative tool to prevent the free electrons from the pump roller (612) from localizing into one area, as shown in FIG. 8A. Since the outer coating layer (604) is still slightly conductive, and not as insulating as the inner layer (602), electrons will not remain static but will instead dissipate as shown in FIG. 8B. Since this is a dissipative method, therefore preventing buildup of electrons instead of flowing them elsewhere, the irrigation tube (600) may not need to be electrically grounded. Therefore, the outer coating layer (604) can be minimal. The conductivity of the outer coating layer (604), such as is provided by PEDOT:PSS, allows for static charges (614) to have a flow pathway, while the transparency of the combination of the inner layer (602) and the outer coating layer (604) allows bubbles to be detected inside the tubing. Further, the elasticity of the combination of the inner layer (602) and the outer coating layer (604) gives the irrigation tube (600) the ability to bend and strain.

IV. EXEMPLARY SEMI-CONDUCTIVE INTERMEDIARY LAYER(S) ON IRRIGATION TUBING TO REDUCE PUMP-GENERATED ECG NOISE

As described above, electrical noise may be problematic in certain environmental conditions for both therapeutic and diagnostic devices. For example, in some catheter systems, electrical static buildup and discharge can occur on the connected irrigation tube (e.g., conduit (40) shown in FIG. 1) due to the irrigation tube contacting moving portions of the system, such as the rollers of a pump (e.g., pump (44) shown in FIG. 1). The buildup and discharge of static electricity can, in some instances, create noise in the RF system at a repeating harmonic consistent with the flowrate of the irrigation pump. Such static-related noise may adversely affect readings from the EP mapping electrodes (e.g., microelectrodes (138) shown in FIGS. 2 and 3). In addition, or in the alternative, such static-related noise may adversely affect signals generated by one or more sensors (e.g., navigation sensor assembly (150) shown in FIGS. 3 and 4). In addition, or in the alternative, such static-related noise may adversely affect delivery of ablation RF energy via ablation electrodes (e.g., cylindraceous body (156) shown in FIGS. 2 through 4).

FIGS. 9-10 depict another example of a medical irrigation tube (900), which may be used with a variation of the catheter assembly (100) of FIG. 1. For example, irrigation tube (900) may be used in place of fluid conduit (40), and may similarly couple with a pump (e.g., pump (44)) to transport irrigation fluid from a fluid source (e.g., fluid source (42)) to a patient (PA). Irrigation tube (900) of this example includes multiple flexible material layers, including a base or inner layer (902), an intermediary layer (904), and an outer coating layer (906). In some versions, the entire inner layer (902) and outer coating surface (906) may be formed as electrical insulators and each be electrically isolated from the exterior of the irrigation tube (900). In some versions, the inner layer (902) and outer coating layer (906) may include of one or more insulating layers which include distinctively different materials. The inner layer (902) may be, for example, extruded or otherwise manufactured to form a hollow cylindrical tube defining a central longitudinal axis (908). The hollow inner portion (910) can function as a lumen or irrigation channel to transport fluid, such as between fluid source (42) and patient (PA).

While the inner layer (902) and outer coating layer (906) may include materials having insulating characteristics, a semi-conductive surface may completely form the intermediary layer (904) of the irrigation tubing, or may stretch only the length of the irrigation tube (900) where the pump rollers (502) come into contact with the irrigation tube (900). By utilizing a semi-conductive material for the intermediary layer (904), such as a material having a resistance ranging from about 100 kΩ to about 1 MΩ, electrical charges on the outer coating surface (906) of the irrigation tube (900) can be electrically grounded and the risk of shock can be minimized. However, in some versions, a conductive intermediary layer (904) may be used if the inner (902) and outer layers (906) of the irrigation tube (900) have sufficient electrical insulation. In other versions, the conductive or semi-conductive intermediary layer (904) may be connected to a grounding cable.

In other versions, the irrigation tube (900) can include three layers of differing materials for the entire length of the irrigation tube (900). For example, one or more semi-conductive layers may include a coating or braiding; or can be co-extruded over the inner layer (902). The semi-conductive layers may also have antistatic properties, in addition to being semi-conductive. In this embodiment, the conductive layer may be electrically connected to a grounding cable for additional noise reduction.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising a catheter, the catheter comprising: (a) a flexible outer sheath defining a first lumen; and (b) a flexible irrigation tube positioned inside the first lumen and including: (i) an inner layer formed of a synthetic polymer compound, the inner layer having a uniform cross-section and a hollow interior, the hollow interior defining a second lumen, and (ii) an outer coating layer disposed around the inner layer, the outer coating layer being formed of a polymeric compound, the polymeric compound including a first polymer or ionomer configured to carry a positive electric charge and a second polymer or ionomer configured to carry a negative electric charge; the second lumen being configured to transport a fluid.

Example 2

The apparatus of Example 1, the combined inner layer and outer coating layer of the flexible irrigation tube being configured to be at least partially optically transmissive such that the fluid is visible through the combined inner layer and outer coating layer.

Example 3

The apparatus of any one or more of Examples 1-2, the synthetic polymer compound of the inner layer including polyvinyl chloride (PVC).

Example 4

The apparatus of any one or more of Examples 1-3, the outer coating layer of the flexible irrigation tube comprising a conductive polymer.

Example 5

The apparatus of any one or more of Examples 1-4, the first polymer or ionomer of the polymeric compound of the outer coating layer being poly(3,4-ethylenedioxythiophene).

Example 6

The apparatus of any one or more of Examples 1-5, the second isomer polymer or ionomer of the polymeric compound of the outer coating layer being poly(styrenesulfonate).

Example 7

The apparatus of any one or more of Examples 1-6, the outer coating layer comprising poly(3,4-ethylenedioxythiophene)-poly(styrenesulfonate).

Example 8

The apparatus of any one or more of Examples 1-7, the outer coating layer having an optical transmissivity from approximately 65% to approximately 90%.

Example 9

The apparatus of any one or more of Examples 1-8, the outer coating layer being at least partially elastic.

Example 10

The apparatus of any one or more of Examples 1-9, the apparatus further comprising a peristaltic pump having two or more pump rollers, the flexible irrigation tube being configured to be coupled to the peristaltic pump and be deformed by each of the two or more pump rollers.

Example 11

The apparatus of Example 10, the outer coating layer of the flexible irrigation tube being configured as a pathway for free electrons to move from the peristaltic pump to a grounding element.

Example 12

The apparatus of any one or more of Examples 1-11, the flexible irrigation tube further comprising a wear-resistive coating disposed around a portion of the outer coating layer, the wear-resistive coating being formed of a polymer.

Example 13

The apparatus of Example 12, the wear-resistive coating being formed of polyurethane.

Example 14

The apparatus of Example 12, the wear-resistive coating being formed of polyolefin.

Example 15

The apparatus of any one or more of Examples 1-14, the catheter further comprising an end effector positioned at a distal end of the catheter, the end effector including one or more radio frequency electrodes configured to ablate tissue.

Example 16

The apparatus of Example 15, the end effector of the catheter further comprising at least one mapping electrode, the at least one mapping electrode being configured to receive electrical potentials from tissue.

Example 17

The apparatus of any one or more of Examples 15-16, the end effector of the catheter further comprising a plurality of openings, the plurality of openings being configured to expel the fluid transported through the second lumen.

Example 18

A medical tube, comprising: (a) an inner layer formed of synthetic polymer compound, the inner layer having a uniform cross-section and a hollow interior, the hollow interior defining a lumen; (b) an outer coating layer disposed around the inner layer, the outer coating layer being formed of a polymeric compound, the polymeric compound including: (i) a first polymer or ionomer configured to carry a positive electric charge, and (ii) a second polymer or ionomer configured to carry a negative electric charge; the lumen being configured to transport a fluid; and the combined inner layer and outer coating layer being configured to be transparent such that the fluid is visible through the combined inner layer and outer coating layer.

Example 19

The medical tube of Example 18, the outer coating layer being poly(3,4-ethylenedioxythiophene)-poly(styrenesulfonate).

Example 20

The medical tube of any one or more of Examples 18-19, the outer coating layer having an optical transmissivity from approximately 65% to approximately 90%.

Example 21

The medical tube of any one or more of Examples 18-20, further comprising a wear-resistive coating disposed around a portion of the outer coating layer, the wear-resistive coating being formed of a polymer.

Example 22

The medical tube of Example 21, the wear-resistive coating being formed of polyurethane.

Example 23

The medical tube of Example 21, the wear-resistive coating being formed of polyolefin.

Example 24

A method of manufacturing a medical tube, comprising: (a) extruding an inner tube layer from a synthetic polymer compound, the inner tube layer having a uniform cross-section and a hollow interior, the hollow interior defining a lumen configured to transport a fluid; (b) providing an outer coating layer to surround the entire the inner tube layer, the outer coating layer being formed of a polymeric compound, the polymeric compound including a first polymer or ionomer configured to carry a positive electric charge a second polymer or ionomer configured to carry a negative electric charge, the combined inner layer and outer coating layer being configured to be optically transmissive such that the fluid is at least partially visible through the combined inner layer and outer coating layer; and (c) providing a wear-resistive coating to surround a portion of the outer coating layer, the wear-resistive coating being formed of a polymer.

Example 25

The method of Example 24, the synthetic polymer compound being comprised of polyvinyl chloride.

Example 26

The medical tube of any one or more of Examples 24-25, the outer coating layer being comprised of poly(3,4-ethylenedioxythiophene)-poly(styrenesulfonate).

Example 27

The method of any one or more of Examples 24-26, the wear-resistive coating being comprised of one of polyurethane or polyolefin.

Example 28

An apparatus comprising a catheter, the catheter comprising: (a) an inner tube comprised of a first flexible material, the inner tube having an inner surface defining a lumen configured to transport a fluid, the first flexible material being electrically nonconductive; (b) an intermediary layer disposed around the inner tube, the intermediary layer comprised of a second flexible material, the second flexible material being electrically conductive; and (c) an outer layer disposed around the intermediary layer, the outer layer comprised of a third flexible material, the third flexible material being electrically nonconductive.

Example 29

The apparatus of claim 28, the second flexible material of the intermediary layer having an electrical resistance from approximately 100 kΩ to approximately 1 MΩ.

Example 30

The apparatus of any one or more of Examples 28-29, the second flexible material of the intermediary layer being electrically semi-conductive.

Example 31

The apparatus of any one or more of Examples 28-30, the apparatus further comprising a peristaltic pump having two or more pump rollers, the catheter being configured to be coupled to the peristaltic pump and deformable by each of the two or more pump rollers.

Example 32

The apparatus of any one or more of Examples 28-31, the catheter further comprising an end effector positioned at a distal end of the catheter, the end effector including one or more radio frequency electrodes configured to ablate a tissue.

Example 33

The apparatus of Example 32, the end effector of the catheter further comprising at least one mapping electrode, the at least one mapping electrode being configured to receive electrical potentials from the tissue.

Example 34

The apparatus of any one or more of Examples 32-33, the end effector of the catheter further comprising a plurality of openings, the plurality of openings being configured to expel a fluid from the lumen.

VI. MISCELLANEOUS

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A catheter, comprising:
   an elongated catheter body having at least one lumen extending therethrough;
   an end effector at a distal end of the elongated catheter body, the end effector comprising one or more openings;
   a flexible irrigation tube extending through the at least one lumen of the catheter body, and having a distal end in fluid communication with the end effector and a proximal end extending out a proximal end of the catheter body and in communication with a source of irrigation fluid, the irrigation tube comprising concentric inner and outer tubing layers:
      the inner tubing layer comprising a synthetic polymer compound and having a uniform cross-section and a hollow interior configured to convey the irrigation fluid from the source of irrigation fluid to the end effector and out through the one or more openings, and
      the outer tubing layer comprising a polymeric composition, the polymeric composition comprising a first polymer configured to carry a positive electric charge and a second polymer configured to carry a negative electric charge.

2. The catheter of claim 1, the combined inner tubing layer and outer tubing layer of the flexible irrigation tube being configured to be at least partially optically transmissive such that the irrigation fluid is visible through the combined inner tubing layer and outer tubing layer.

3. The catheter of claim 1, the synthetic polymer compound of the inner tubing layer including polyvinyl chloride (PVC).

4. The catheter of claim 1, the outer tubing layer of the flexible irrigation tube comprising a conductive polymer.

5. The catheter of claim 1, the first polymer of the polymeric composition of the outer tubing layer being poly(3,4-ethylenedioxythiophene).

6. The catheter of claim 1, the second polymer of the polymeric composition of the outer tubing layer being poly(styrenesulfonate).

7. The catheter of claim 1, the polymeric composition of the outer tubing layer comprising poly(3,4-ethylenedioxythiophene)-poly(styrenesulfonate).

8. The catheter of claim 1, the outer tubing layer having an optical transmissivity from approximately 65% to approximately 90%.

9. The catheter of claim 1, the outer tubing layer being at least partially elastic.

10. The catheter of claim 1, the end effector including one or more electrodes configured to ablate tissue or to receive electrical potentials from tissue.

11. The catheter of claim 1, the end effector of the catheter comprising a dome tip electrode comprising the plurality of openings, the plurality of openings being configured to expel the irrigation fluid received in the dome tip electrode from the irrigation tube.

12. The catheter of claim 1, the proximal end of the flexible irrigation tube being coupled to a peristaltic pump having two or more pump rollers, the flexible irrigation tube being configured to be deformed by each of the two or more pump rollers.

13. The catheter of claim 12, the outer tubing layer of the flexible irrigation tube being configured as a pathway for free electrons to move from the peristaltic pump to a grounding element.

14. The catheter of claim 1, the flexible irrigation tube further comprising a wear-resistive coating disposed around a portion of the outer tubing layer, the wear-resistive coating being formed of a polymer.

15. The catheter of claim 14, the wear-resistive coating being formed of polyurethane or polyolefin.

16. A catheter, comprising:
   an elongated catheter body having at least one lumen extending therethrough;
   an end effector at a distal end of the elongated catheter body, the end effector comprising one or more openings;
   a flexible irrigation tube extending through the at least one lumen of the catheter body, and having a distal end in fluid communication with the end effector and a proximal end extending out a proximal end of the catheter body and in communication with a source of irrigation fluid, the irrigation tube comprising concentric inner and outer tubing layers:
      the inner tubing layer comprising a synthetic polymer compound and having a uniform cross-section and a hollow interior configured to convey the irrigation fluid from the source of irrigation fluid to the end effector and out through the one or more openings;

the outer tubing layer comprising a polymeric composition, the polymeric composition comprising a first polymer configured to carry a positive electric charge and a second polymer configured to carry a negative electric charge; and the combined inner tubing layer and outer tubing layer being transparent such that the fluid is visible through the combined inner tubing layer and outer tubing layer.

17. A catheter, comprising:

an elongated catheter body having at least one lumen extending therethrough;

an end effector at a distal end of the elongated catheter body, the end effector comprising one or more openings;

a flexible irrigation tube extending through the at least one lumen of the catheter body, and having a distal end in fluid communication with the end effector and a proximal end extending out a proximal end of the catheter body and in communication with a source of irrigation fluid, the irrigation tube comprising concentric inner and outer tubing layers:

the inner tubing layer formed entirely of an insulating synthetic polymer and having a uniform cross-section and a hollow interior configured to convey the irrigation fluid from the source of irrigation fluid to the end effector and out through the one or more openings, and the outer tubing layer formed entirely of a conductive polymeric composition, the conductive polymeric composition comprising a first polymer configured to carry a positive electric charge and a second polymer configured to carry a negative electric charge.

18. The catheter of claim 17, the flexible irrigation tube further comprising a wear-resistive coating disposed around a portion of the outer tubing layer, the wear-resistive coating being formed of a polymer.

19. The catheter of claim 17, the proximal end of the flexible irrigation tube being coupled to a peristaltic pump having two or more pump rollers, the flexible irrigation tube being configured to be deformed by each of the two or more pump rollers.

20. The catheter of claim 19, the outer tubing layer of the flexible irrigation tube being configured as a pathway for free electrons to move from the peristaltic pump to a grounding element.

\* \* \* \* \*